United States Patent [19]
Ashby

[11] Patent Number: 5,108,445
[45] Date of Patent: Apr. 28, 1992

[54] PROSTHETIC BEARING ASSEMBLY

[75] Inventor: Alan Ashby, Maidenhead, England

[73] Assignee: Pfizer Hospital Products Group, Inc., New York, N.Y.

[21] Appl. No.: 633,712

[22] Filed: Dec. 21, 1990

[30] Foreign Application Priority Data

Jan. 4, 1990 [GB] United Kingdom ............... 9000124

[51] Int. Cl.$^5$ ............................................. A61F 2/34
[52] U.S. Cl. ................................................... 623/11
[58] Field of Search ..................... 623/22, 16, 18, 19, 623/20, 23

[56] References Cited

U.S. PATENT DOCUMENTS

| | | | |
|---|---|---|---|
| 4,324,006 | 4/1982 | Charnley | 632/22 |
| 4,563,778 | 1/1986 | Roche et al. | 623/22 |
| 4,566,138 | 1/1986 | Lewis et al. | 623/22 |
| 4,676,798 | 6/1987 | Noiles | 623/22 |
| 4,695,282 | 9/1987 | Forte et al. | 623/22 |
| 4,704,127 | 11/1987 | Averill et al. | 623/22 |
| 4,769,041 | 9/1988 | Morscher | 623/22 |
| 4,795,469 | 1/1989 | Oh | 623/22 |
| 4,919,675 | 4/1990 | Dietschi | 623/22 |
| 4,955,919 | 9/1990 | Pappas et al. | 623/22 |
| 4,960,427 | 10/1990 | Noiles | 623/22 |

FOREIGN PATENT DOCUMENTS 2117646 4/1982 United Kingdom .

Primary Examiner—David Isabella
Attorney, Agent, or Firm—Peter C. Richardson; Lawrence C. Akers; Raymond W. Augustin

[57] ABSTRACT

A prosthetic acetabular cup 100 includes a fixation element 102 for introduction into the acetabulum. The fixation element 102 has a concave inner surface with a generally circular base formed in a plane generally perpendicular to the central longitudinal axis. A bearing component 7 is formed from a deformable material and has a concave opening therein for receiving a spherical head of a prosthetic femoral component. The bearing component 7 has an outer surface that nests within the concave inner surface of the fixation element 102. A snap lock mechanism is used to lock the bearing component 7 within the fixation element 102 in the axial direction. Both the fixation element 102 and the bearing component 7 include a plurality of circumferentially spaced recesses 3, 12 located around a common pitch circle adjacent the generally circular base of the fixation element 102. When aligned, the recesses 3, 12 form a combined recess of predetermined shape for receiving a pin 20 which is inserted therein to prevent relative rotation between the bearing component and the fixation element.

8 Claims, 5 Drawing Sheets

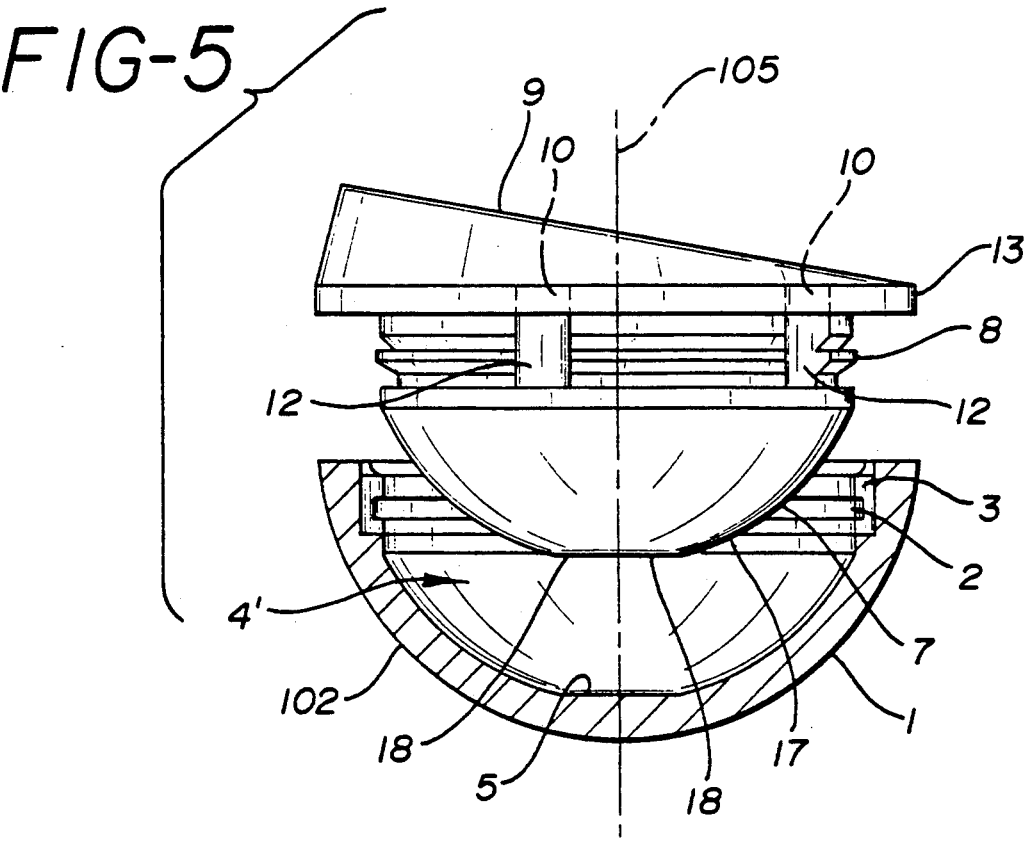
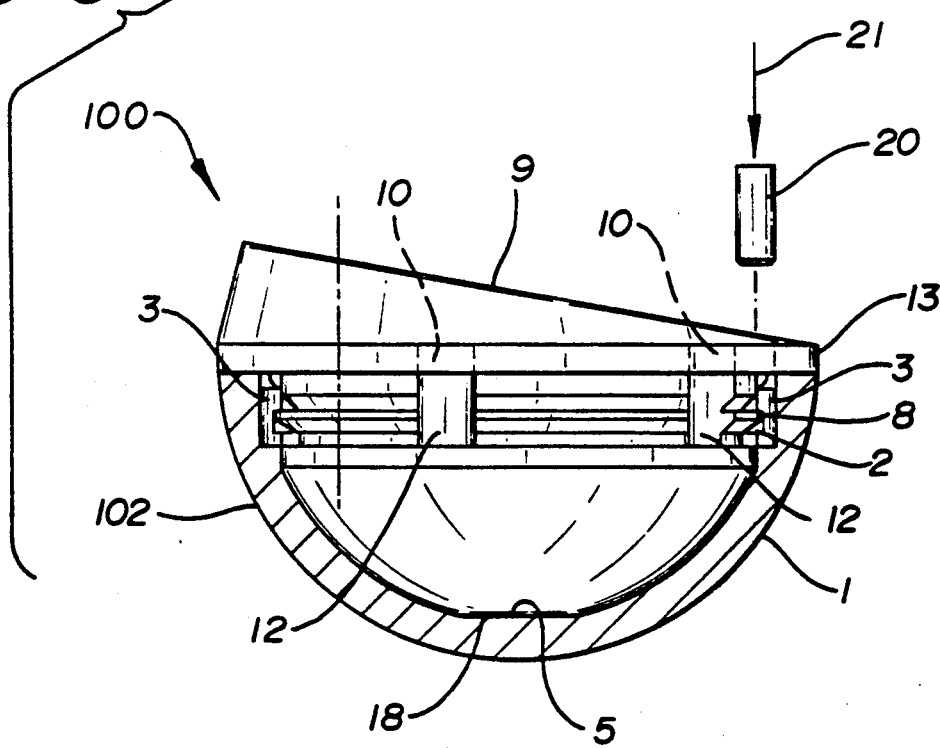

PROSTHETIC BEARING ASSEMBLY

BACKGROUND OF THE INVENTION

1. Field of the Invention

This invention relates to a prosthetic bearing assembly of the kind comprising an outer fixation element and an inner bearing component. Bearing assemblies of this type are used in various orthopedic prostheses and the present invention is particularly, although not exclusively, applicable for use with prosthetic acetabular cups.

2. Description of the Prior Art

The use of prosthetic implant devices in the human body for replacing defective, damaged or diseased anatomical joints of the body has become quite well known. One of the more common forms of implant devices is the hip joint prosthesis which provides an interconnection between the femur and the acetabular socket of the pelvis. Conventional prosthetic hip joints usually include an artificial femoral component having a spherical head member which is received within a complementary spherical socket provided by an acetabular cup assembly.

One frequently used form of acetabular cup assembly has a metal shell component, which is secured to the acetabulum, and a bearing insert component, usually constructed of plastic, secured within the metal shell component to complete the cup assembly. It has been suggested that the bearing insert component be assembled with the shell component interoperatively; that is, the shell component is seated permanently within the acetabulum and then the bearing insert component is inserted into the shell component by the surgeon, thereby providing the surgeon with an opportunity, during implantation, to assess the cup assembly position and hip joint function using provisional trials and enabling minor adjustments prior to commitment to a final implant position. Thus, the bearing insert component is provided with a bearing face which is angled slightly relative to the lower face of the shell component so that by rotation of the bearing insert component relative to the shell component, the orientation and anteversion of the bearing face can be adjusted after seating of the shell component and prior to permanent assembly of the bearing insert component with the shell component.

Prosthetic acetabular cups are known which use a snap-fit between the shell and the bearing or other methods for preassembly of bearing components of different internal diameters. For example, U.S. Pat. No. 4,695,282 shows an acetabular cup assembly which includes an outer metal fixation shell and a plastic bearing insert which is snapped into position. The arrangement is such that the shell can be repositioned circumferentially to a limited number of positions relative to the metal shell. U.S. Pat. No. 4,676,798 also shows a socket bearing assembly in which the shell can be located in different circumferential positions. A disadvantage with this latter construction is that the number of alternative positions is limited and the construction is expensive to manufacture due to the intricacy of the various components.

SUMMARY OF THE INVENTION

It is an object of the present invention to provide a prosthetic bearing assembly having geometric features which allow for a more precise control of the relative orientation between the outer shell and the bearing component.

It is yet another object of the invention to provide an acetabular cup assembly in which the bearing component can be securely locked into position with regard to the outer shell fixation element.

It is yet an additional object of the invention to provide a prosthetic bearing assembly wherein the bearing component can be prevented from rotating within the fixation element via a pin inserted into any one of a plurality of recesses formed therebetween.

These and related objects are achieved in the present invention by a prosthetic acetabular cup which has a fixation element adapted to be implanted into the acetabulum. The fixation element has a concave inner surface with a generally circular base formed about a first longitudinal axis. A bearing component is formed from a deformable material and has a concave opening therein formed about a second longitudinal axis for receiving the spherical head of a prosthetic femoral component. The bearing component has an outer surface that nests within the concave inner surface of the fixation element with its second axis angularly offset from the first axis through the fixation element. The bearing component is locked within the fixation element in the axial direction by a snap lock mechanism.

A plurality of circumferentially spaced recesses are formed on both the fixation element and the bearing component around a common pitch circle located adjacent the base of the fixation element. A recess in the fixation element and a recess in the bearing component form a combined recess of predetermined shape. A locking element in the form of a pin which has a shape corresponding to the predetermined shape of the combined recess is inserted therein so as to prevent relative rotation between the bearing component and the fixation element.

The use of a separate location element such as a pin enables the assembly to be relatively simple and the vernier adjustment provided allows a more accurate control of the adjustable relative positions. Preferably, a number of recesses defining first location positions are provided on a pitch circle diameter on the fixation element and a number of recesses defining second location positions on the same pitch circle diameter are located on the bearing component. The number of locking locations on the bearing component differ by at least a single unit from those on the fixation element, i.e. there are more recesses formed on one of the fixation elements and bearing elements than on the other. The locking pin extends between a first location position on the fixation element and a second location position on the bearing component.

The location positions can be substantially equispaced around the corresponding pitch circle diameters on the fixation element and the bearing component. Alternatively, the location positions can be spaced around a sector of an arc of the pitch circle diameter on the fixation element and the bearing component. This would be done to provide a finer adjustment in a sector of the pitch diameter.

Since this arrangement the number of positions is different by at least a single unit, it allows for a large number of different orientation assembly positions. As the number of holes in the fixation element and bearing element is different by, for example, a single unit, the number of holes of one component is N+1 and the other is N. This allows the number of assembled orientations of N×N+1, thus providing, what is in effect, a vernier adjustment, i.e. a fine adjustment between the circumferential position of the angled recess of the bearing component and the shell or fixation element.

The location positions may conveniently be provided by mating openings and/or sockets formed in the bearing component and the fixation element, with the locking element in the form of an interlocking pin corresponding in cross-section to the opening formed. It will be seen therefore that while this construction allows for substantially finer control of the orientation of the assembly than previous arrangements, this is achieved with a significantly lower manufacturing cost.

The invention also includes a prosthesis incorporating the prosthetic bearing assembly as set forth above.

BRIEF DESCRIPTION OF THE DRAWINGS

The invention can be performed in various ways and some embodiments will now be described by way of example and with reference to the accompanying drawings in which similar reference numerals represents similar elements throughout the several views:

FIG. 5 is a partial side elevation showing the bearing component and a cross-sectional view of the fixation element prior to assembly;

FIG. 6 is a side view of the bearing component and a cross-sectional view of the fixation element after assembly with the location pin ready for insertion;

DESCRIPTION OF THE PREFERRED EMBODIMENT

Figure 1:
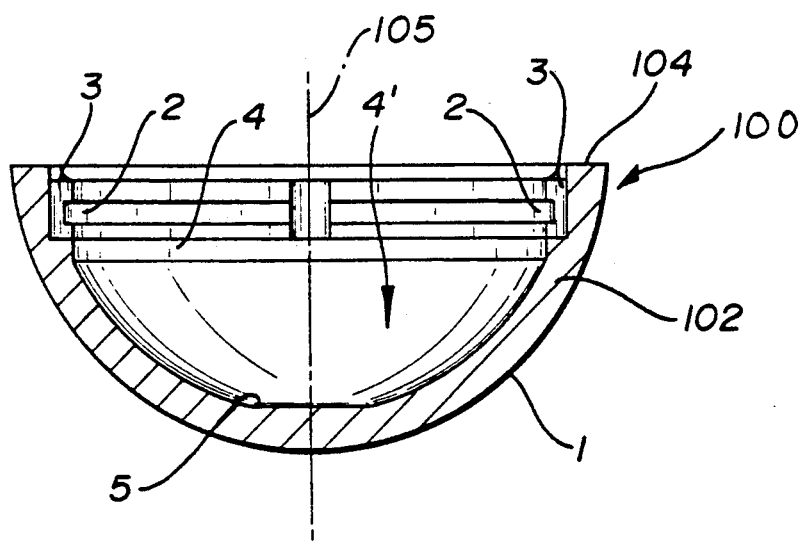
FIG. 1 is a cross-sectional view through a fixation element in the form of an acetabular cup shell embodying the present invention.

Referring to FIGS. 1-6, the bearing assembly generally denoted as 100 which comprises a fixation element generally denoted as 102 for attachment to the available anatomy and in the example shown is for use in an acetabular hip joint. FIG. 1 shows fixation element 102 in the form of an acetabular cup shell 1 embodying the invention. As is well known, shell 1 is made from any suitable material, for example, a synthetic plastics material or metal and may have any suitable exterior surface finish or fittings to enable it to be located in position on the available anatomy. In the case of an acetabular cup, shell 1 is generally hemispherical in shape with a central axis 104. This shell 1 has a retaining groove 2 to enable it to retain an inner bearing component in a manner to be described. As will be seen from FIG. 1, the preferred groove 2 is of simple square or rectangular cross-section.

Figure 2:
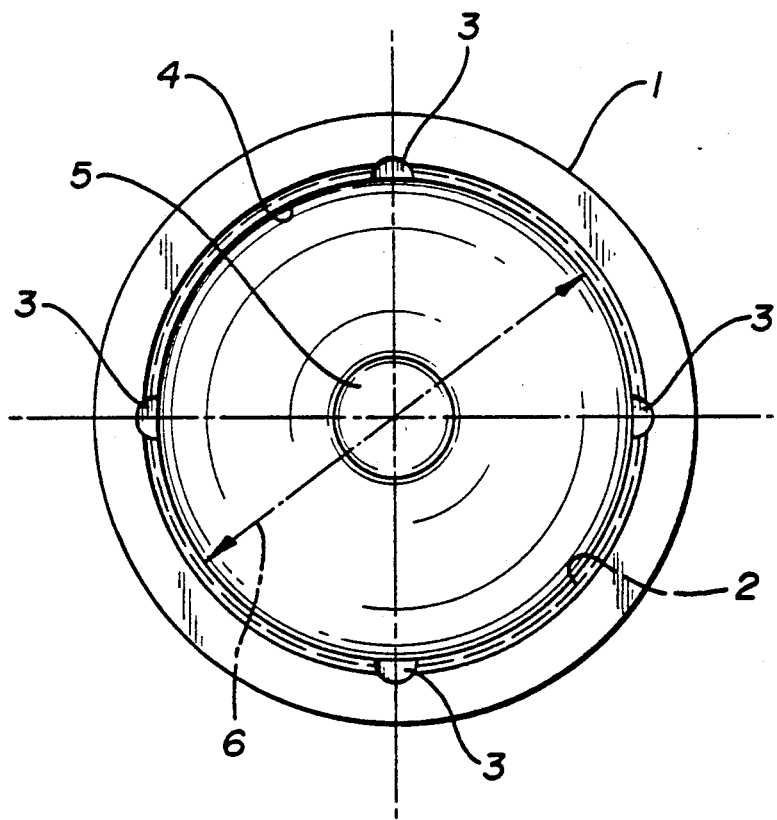
FIG. 2 is a plan view of the cup shell shown in FIG. 1.

In the preferred embodiment, four location recesses 3 are also provided and which are in the form of semicircular blind holes as is most clearly seen in FIG. 2. These recesses extend into a cylindrical throat portion 4 of the hemispherical opening 4', of shell 1. The inner surface of opening 4', also has a flat polar area indicated by reference numeral 5. Broken line 6 indicates the pitch circle diameter of the recesses 3.

Figure 3:
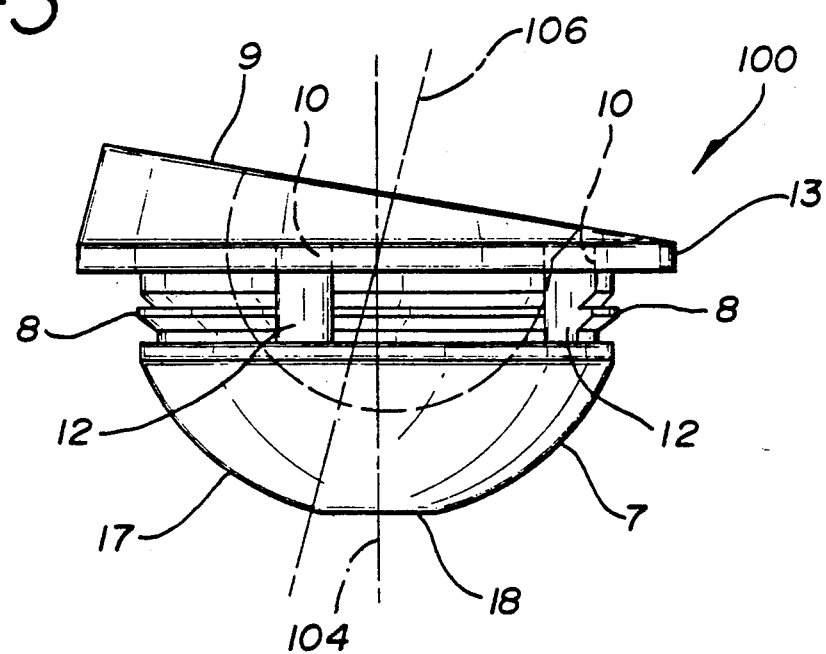
FIG. 3 is a side elevation of a snap-fit bearing component for use in the shell shown in FIGS. 1 and 2.
Figure 4:
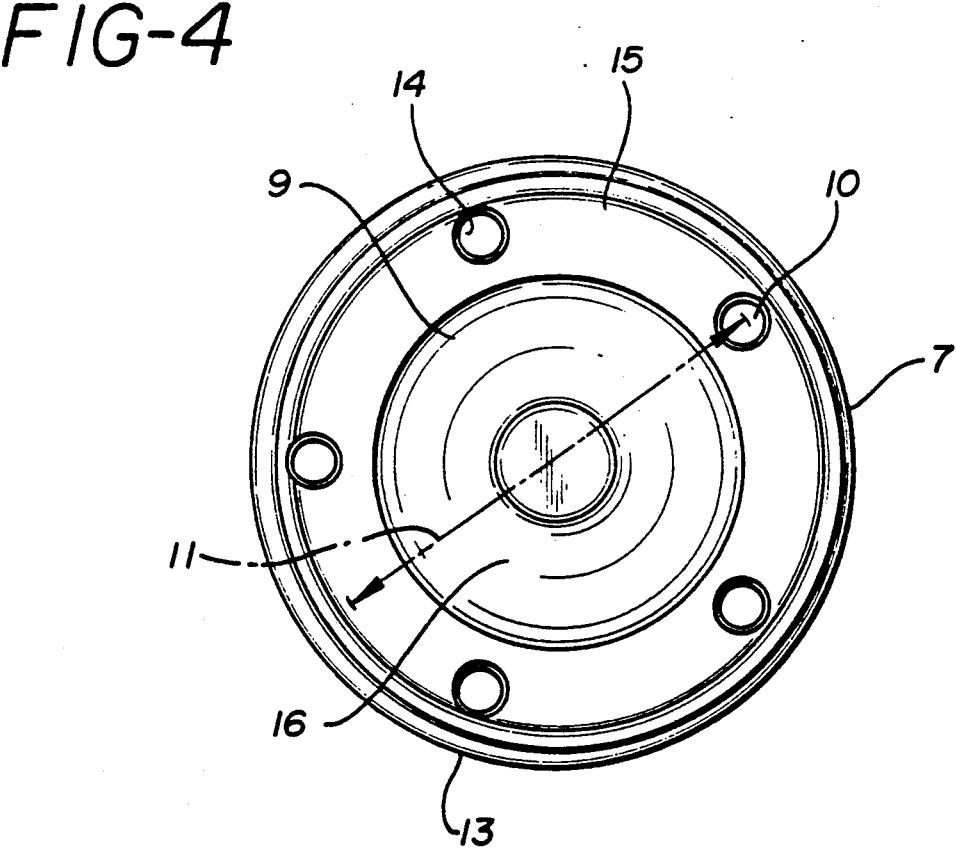
FIG. 4 is a plan view of the bearing component shown in FIG. 3.

FIGS. 3 and 4 show an inner substantially circular bearing component 7 having an outer surface which nests the opening 4', of shell 1. This bearing component is snap-fit in the shell in a well known manner and has an external diameter which is generally equivalent, and slightly smaller than the internal surface of shell 1. This allows the assembly of the two components in the manner shown in FIG. 5. Bearing component 7 is preferably made from a synthetic plastic material such as ultra high molecular weight polyethylene and is provided with a deflectable fin 8 which is deflected on insertion of the bearing component into the shell and subsequently engages itself in the circular slot 2 therein to produce the "snap-fit" which holds the assembly in the axial direction.

The concave opening 4' of the front bearing face 9 articulates with the spherical head of a prosthetic femoral hip component (not shown). In general, bearing 7 consists of a hemispherical female form with a cylindrical throat. The access to the throat is generally in the polar direction with respect to the assembly. In the preferred embodiment, front face 9 is angled with respect to axis 105 and the plane of base 104 of shell 1. Alternatively, face 9 may be perpendicular to the polar axis if the axis of the throat and axis 106 is angled thereto. As will be seen from FIG. 4, five holes 10 are provided on a pitch circle diameter 11 which is the same as the pitch circle diameter 6 as shown on the shell in FIG. 2. The holes 10 emerge as half-cylindrical shaped recesses 12 in the side of the bearing component as shown in FIG. 3. The holes 10 are provided in a flange 13 at the outer rim of the component.

The recesses are located as far as possible from the bearing wear surfaces on the internal diameter of the plastic material component, thus having the least effect on the available plastic wear thickness. The holes are also counter-bored as indicated by reference numeral 14 from the outer face 15 of a component to allow either for the location of the pin inserter (to be described) or to help locate the pin to be inserted.

As shown in FIG. 4, the surface 9 includes a socket 16 and may have a longitudinal axis 105 which is angularly offset from axis 104 to accommodate an anteversion of the head of a femoral prosthesis (not shown). Socket 16 may have a generally hemispherical shape and is slightly off-center from the flange 13. The outer surface of the bearing component 17 which mates with and nests inside the inner surface of the shell also has a flat polar area indicated by reference numeral 18.

FIG. 5 shows the bearing component about to be fitted into the shell and FIG. 6 shows them in the assembled position. The deflectable fin 8 is now located in the groove 2 and prevents axial removal of the bearing component. Subject to resistance provided by friction, it is possible to rotate the orientation of the bearing component in relation to the shell 1. As the holes 10 and recesses 12 are on the same pitch circle diameter as the recesses 3, the parts can be rotated so that one of the recesses 12 aligns with one of the recesses 3 to provide a completely circular combined recess. Of course, the combined recess may be of any predetermined shape.

FIG. 6 also shows the separate location means, which in this case is in the form of a pin 20 which acts as a locking means and is positioned to extend between a first location position provided by recess 3 on the fixation element provided by the shell and a second location position formed by the holes 10 in flange 9 and recesses 12 on the bearing component. In order to achieve this the pin 20 is pushed through one of the holes 10, which is aligned with one of the recesses 3, and into the combined circular recess provided by the recess 3 and the recess 12. The direction of movement of the pin 20 to provide insertion is indicated by arrow 21. Pin 20 is dimensioned so that it closely fills the combined circular recess and thus locks the bearing component and the shell against relative circumferential movement.

The relative positions between the bearing component and the fixation element are determined intraoperatively prior to insertion of the pin 20. As preferred shell 1 has four recesses 3 and preferred bearing component 7 has five recesses 12, it will be appreciated that a vernier dial-like adjustment is provided.

Figure 7:
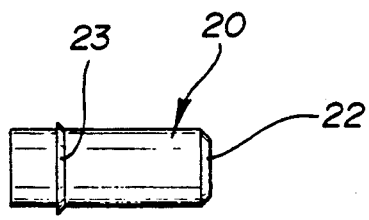
FIG. 7 is a side view of the location pin of the present invention.

FIG. 7 shows one embodiment of a locking pin 20 which is cylindrical and has a chamfer or radiused leading edge 22 to assist in easy insertion. A circumferential deflecting fin 23 is provided which engages on a suitable feature (not shown) in the drawings but, for example, a groove in recesses 12 and 3 to hold the pin in place and prevent it from moving outward in service.

Figure 8:
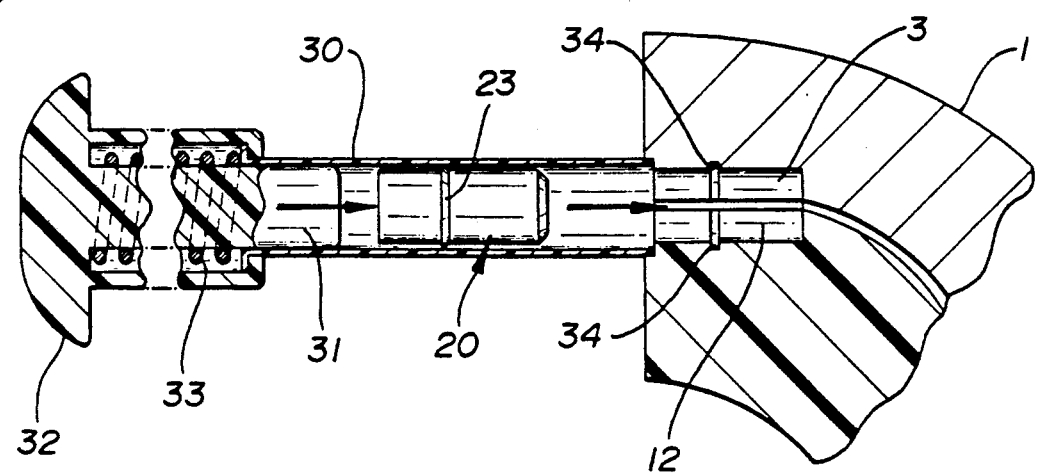
FIG. 8 is a side view of a device partially in cross-section for inserting the pin shown in FIG. 7 in position.

There are various ways of inserting the pin in place. In FIG. 8 the preferred inserter is shown which comprises a tube 30 within which pin 20 can be located. Pin 20 is forced down the tube by a piston 31 operated by a plunger 32 which is biased outwardly by a compression spring 33. Bearing component 7 and shell 1 are shown schematically on the right hand side of the drawing and it will be seen that the inserter complete with pin 20 is located on the combined bore 3, 12 which is to be used and the plunger 32 which is operated to push the pin into place. In this drawing a retaining groove 34 is shown which acts to retain the flange 23 in place and thus prevent pin 20 from working its way out.

Figure 9:
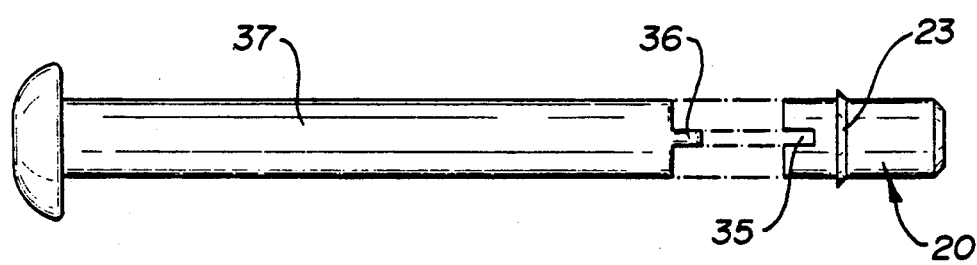
FIG. 9 is an elevation view of an alternative embodiment of a device for inserting the pin of FIG. 7 into position.

FIG. 9 shows another inserter and pin embodiment. In this embodiment the pin 20, is provided with a socket 35, provided with means for locating and holding a tip 36 provided on inserter 37. The device for holding the tip 36 in socket 35 could take various forms, for example, deforming fins could be provided on the cylindrical walls of socket 35 or socket 35 could be of some particular cross-section which mates with the tip 36.

Figure 10:
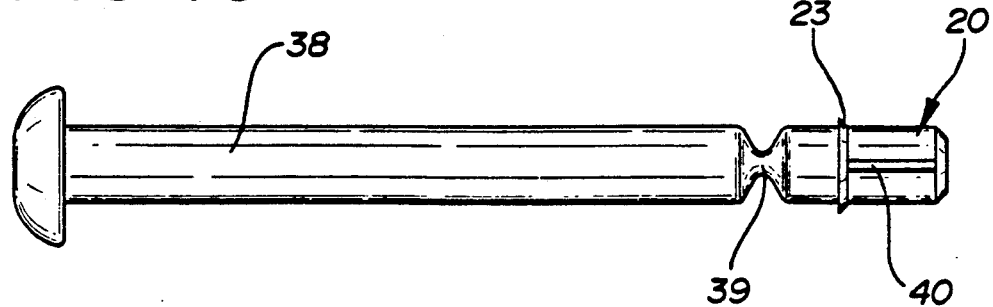
FIG. 10 shows yet another alternative construction of the device.

In the alternate construction for the inserter shown in FIG. 10, a pin 20" and inserter 38 are made from a synthetic plastic material, for example, by injection molding or machining, and the inserter is connected to the pin 20" by a portion of narrowed diameter indicated by reference numeral 39. Thus the inserter can carry the pin and when pin 20" has been located into the assembly, relative rotation of the inserter 38 will cause fracture at the necked down section 39, leaving the pin in position and allowing the inserter 38 to be discarded. To allow this feature to operate, the pin must engage against an anti-rotation feature to insure that the friction of the pin in its eventual resting place is greater than that required to shear narrowed section 39. The anti-rotation feature could, for example, be a projecting key indicated by reference numeral 40 which can engage in a suitable keyway (not shown) provided in one of the recesses 3 or 12 or in one of the holes 10.

The advantage of the assembly 100 of the present invention is that the surgeon can implant the fixation element and then fully seat the bearing component within the fixation element in the axial direction. The surgeon can place the spherical head of the femoral component within the bearing component and rotate the bearing insert to its optimal position. Thereafter, he inserts pin 20 to lock the parts from relative rotation.

Figure 11:
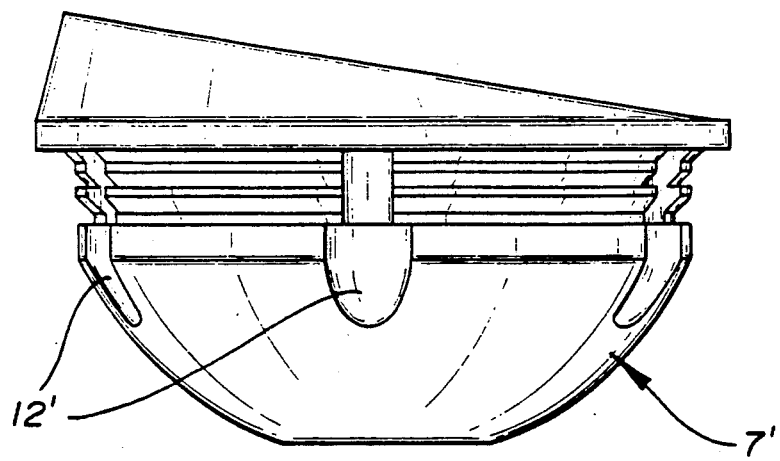
FIG. 11 is a side elevation view of a second embodiment of the snap-fit bearing component of the present invention.
Figure 12:
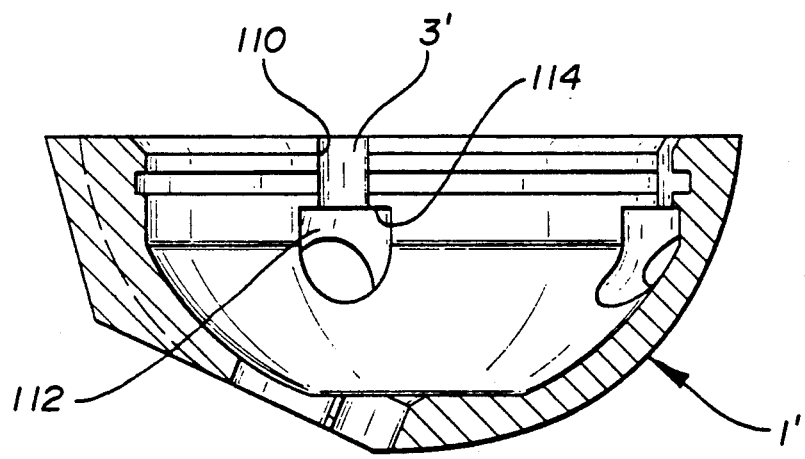
FIG. 12 is a cross-sectional view of a second embodiment of the shell of the present invention.
Figure 13:
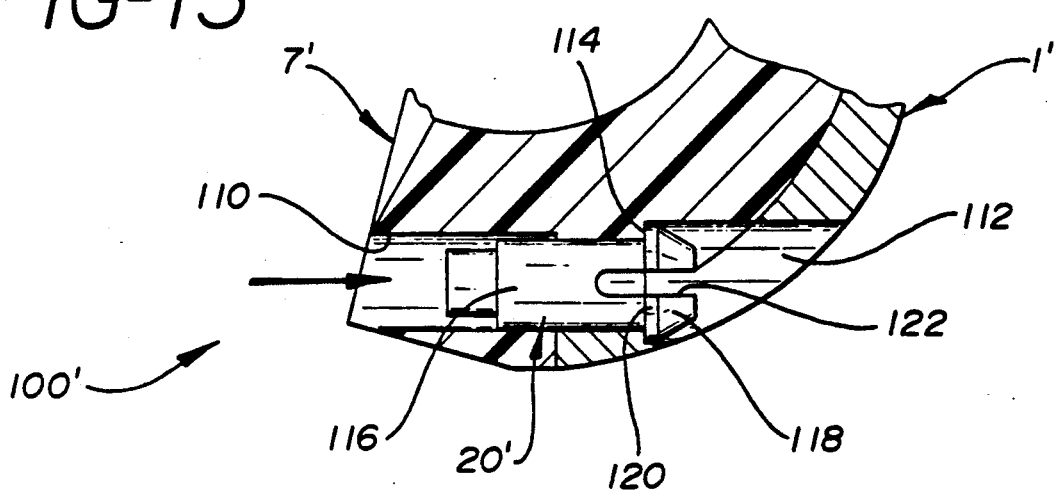
FIG. 13 is a partial cross-sectional view of an assembly of the alternate bearing and shell of FIGS. 11 and 12 with a special pin locking the assembly together.

Referring to FIGS. 11-13, there is shown an alternate embodiment of the bearing assembly of the present invention generally denoted as 100'. Cup 100' consists of a bearing insert 7', which is identical to bearing insert 7 with the exception that there are provided alternately shaped recesses 12' thereon. In addition, an alternate shell 1' is provided which is similar to shell 1 except for recesses 3'. Recesses 3' are shaped to cooperate with recesses 12, to form a combined shape as shown in FIG. 13 having a first generally cylindrical portion 110, an enlarged end portion 112, and a shoulder 114. An alternate pin 20' is provided for insertion into the recess formed by the combined recesses 3' and 12'. Pin 20' has a generally cylindrical body portion 116 and an enlarged forward end portion 118. A shoulder 120 is formed between end portion 118 and generally cylindrical body portion 116. A longitudinally extending slot 122 bisects end 118 and is sufficiently wide and deep to permit forward end 118 to deflect inwardly and fit through cylindrical portion 110. Upon insertion, as shown in FIG. 13, end 118 of pin 20' first deflects inwardly and then snaps out in area 112 of the combined recess so that shoulder 120 engages shoulder 114 to lock the pin in position.

While several examples of the present invention have been described, it is obvious that many changes and modifications may be made thereunto, without departing from the spirit and scope of the invention.

I claim:

1. An implantable bone prosthesis comprising:
   a fixation element for introduction into a bone cavity, said fixation element having a concavity therein with a generally planar base with a plurality of first peripheral recesses formed on an inner peripheral surface thereof open to said generally planar base;
   a bearing component having a means for receiving an articulating member, said bearing component having an outer surface that nests within the concavity of the fixation element and said bearing component further having a base surface, said outer surface having a plurality of second recesses formed therein open to said base surface alignable with the recesses formed on said inner peripheral surface of said fixation element to form a combined recess of predetermined shape, the number of first recesses differing from the number of second recesses by at least one; and
   a locking element having a shape corresponding to said predetermined shape of said combined recess and insertable therein through said base surfaces of said fixation element and said bearing component to prevent relative rotation between said bearing component and said fixation element.

2. The prosthesis as set forth in claim 1 wherein said recesses in said fixation element and said bearing element have an identical semi-circular cross-sectional shape.

3. The prosthesis as set forth in claim 2 wherein said locking element is a cylindrical pin of predetermined length having a cross-section corresponding to the combined circular cross-section of the semi-circular recesses in said fixation element and said bearing component.

4. The prosthesis as set forth in claim 3 wherein said pin includes a means for retaining said pin within said combined recess.

5. The prosthesis as set forth in claim 1 wherein the fixation element is an acetabular shell having a generally hemispherical shape formed about a central axis therethrough.

6. The prosthesis as set forth in claim 4 wherein said means in said bearing component for receiving an articulating bearing member is a generally hemispherical cavity with a base formed in a plane angularly offset from the plan containing the base of said shell.

7. A prosthetic acetabular cup comprising:
a fixation element for introduction into the acetabulum, said fixation element having a concave inner surface with a generally circular base formed in a plane generally perpendicular to a central longitudinal axis;
a non-symmetrical bearing component formed of a deformable material, said bearing component defining a base surface having a concave opening therein for receiving a spherical head of a prosthetic femoral component, said bearing component further having an outer surface that nests within the concave inner surface of said fixation element;
means for locking said bearing component within said fixation element in the axial direction;
means for circumferentially locating said bearing component within said fixation element, said means for locating including a plurality of first location recesses on said fixation element and a plurality of second location recesses on said bearing component alignable with said first location recesses, said number of first location recesses differing from the number of second location recesses by at least one; and
means for locking said bearing component within said fixation element in the circumferential direction insertable through said base surfaces and engageable with said aligned first and second location recesses.

8. A prosthetic acetabular cup as set forth in claim 7 wherein said location recesses on said fixation element and said bearing component comprise;
a plurality of circumferentially spaced recesses formed in both said fixation element and said bearing component around a common pitch circle adjacent said generally circular base of said fixation element, which when aligned, said recesses in said fixation element and said bearing component form a combined recess of predetermined shape open towards said base of said fixation element and said bearing component; and wherein said means for locking said bearing component within said fixation element comprises,
a pin having a shape corresponding to said predetermined shape of said combined recess for insertion therein to prevent relative rotation between said bearing component and said fixation element.

* * * * *